United States Patent
Alpegiani et al.

(10) Patent No.: US 9,315,541 B2
(45) Date of Patent: Apr. 19, 2016

(54) PROCESS FOR THE PREPARATION OF UNSATURATED TRIFLUOROMETHANESULFONATE STEROID DERIVATIVES

(71) Applicant: OLON S.P.A., Rodano (IT)

(72) Inventors: Marco Alpegiani, Rodano (IT); Tania Cristiano, Milan (IT)

(73) Assignee: OLON S.P.A., Rodano (IT)

( * ) Notice: Subject to any disclaimer, the term of this patent is extended or adjusted under 35 U.S.C. 154(b) by 0 days.

(21) Appl. No.: 14/713,314

(22) Filed: May 15, 2015

(65) Prior Publication Data
US 2015/0337007 A1    Nov. 26, 2015

(30) Foreign Application Priority Data
May 20, 2014    (IT) ............................... MI2014A0919

(51) Int. Cl.
| | | |
|---|---|---|
| C07J 43/00 | (2006.01) | |
| C07J 75/00 | (2006.01) | |
| C07J 1/00 | (2006.01) | |
| C07J 31/00 | (2006.01) | |

(52) U.S. Cl.
CPC ............... *C07J 75/00* (2013.01); *C07J 1/0011* (2013.01); *C07J 31/006* (2013.01); *C07J 43/003* (2013.01)

(58) Field of Classification Search
CPC ............................... C07J 43/003; C07J 31/006
See application file for complete search history.

(56) References Cited

U.S. PATENT DOCUMENTS 8,236,946 B2 *    8/2012  Bury ..................... C07J 43/003
                                                    540/95

OTHER PUBLICATIONS

Zaragoza Dorwald, Side Reactions in Organic Synthesis, 2005, WILEY-VCH Verlag GmbH & Co. KGaA, Weinheim, Preface. p. IX.*
Wentworth et al, Organic Letters, A Soluble Polymer-Supported Triflating Reagent: A High-Throughput Synthetic Approach to Aryl and Enol Triflates, 2000, 2(4), pp. 477-480.*

* cited by examiner

*Primary Examiner* — Paul A Zucker
(74) *Attorney, Agent, or Firm* — Silvia Salvadori, P.C.; Silvia Salvadori

(57) ABSTRACT

Disclosed is a method for the conversion of a compound of formula 3 to a compound

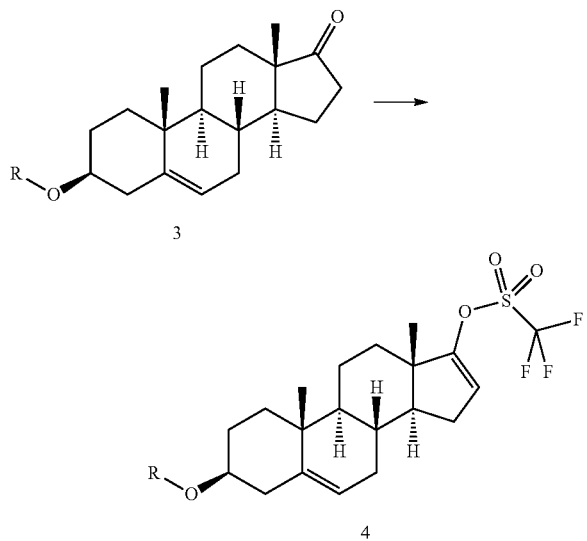

of formula 4, wherein R is an acetyl group or an alcohol-protecting group. The process involves reacting 3 with a triflating agent in the presence of a nicotinate (3-pyridinecarboxylate) of a C1-C4 alcohol, preferably methyl nicotinate (methyl 3-pyridinecarboxylate) or ethyl nicotinate (ethyl 3-pyridinecarboxylate), to give 4. The method can be conveniently used in a process for the preparation of Abiraterone or Abiraterone acetate.

8 Claims, No Drawings

PROCESS FOR THE PREPARATION OF UNSATURATED TRIFLUOROMETHANESULFONATE STEROID DERIVATIVES

This application is a U.S. Non-Provisional Application which claims priority to and the benefit of Italian Patent Application No. MI2014A000919 filed on May 20, 2014, the content of which is incorporated herein by reference in its entirety.

FIELD OF INVENTION

The present invention relates to a novel, improved process for the preparation of unsaturated trifluoromethanesulphonate steroid derivatives (triflates) useful as intermediates in the preparation of Abiraterone and Abiraterone acetate. A key element of the method is the use of a nicotinic acid ester (3-pyridinecarboxylic acid) in the trifluoromethanesulphonation (triflation) step.

BACKGROUND TO THE INVENTION

Abiraterone acetate, the chemical name of which is (3β)-17-(3-pyridinyl)androsta-5,16-dien-3-yl acetate of formula 1, is the prodrug of the active metabolite Abiraterone (2), a selective inhibitor of the enzyme CYP17.

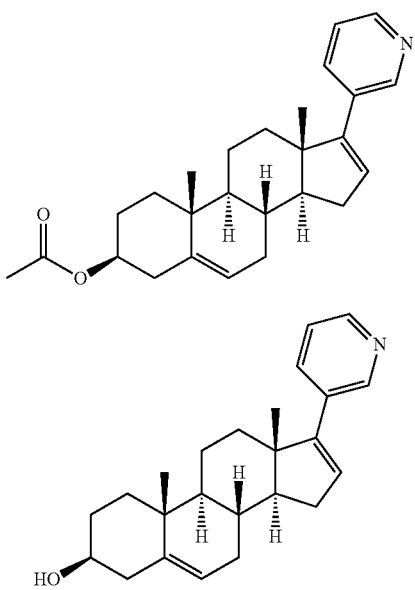

Abiraterone acetate is the active ingredient of the novel medicament Zytiga, which can be administered orally and is indicated, together with prednisone or prednisolone, for the treatment of metastatic castration-resistant prostate cancer.

Numerous processes are reported in the literature for the preparation of Abiraterone or derivatives thereof. In most cases the starting product is prasterone (dehydroepiandrosterone) or a derivative thereof of formula 3, and the key intermediate is a trifluoromethanesulphonate of formula 4 which, by Suzuki reaction with diethyl(3-pyridyl)borane or with 3-pyridylboronic acid leads, optionally after processing of the R group, to the formation of Abiraterone and/or Abiraterone acetate.

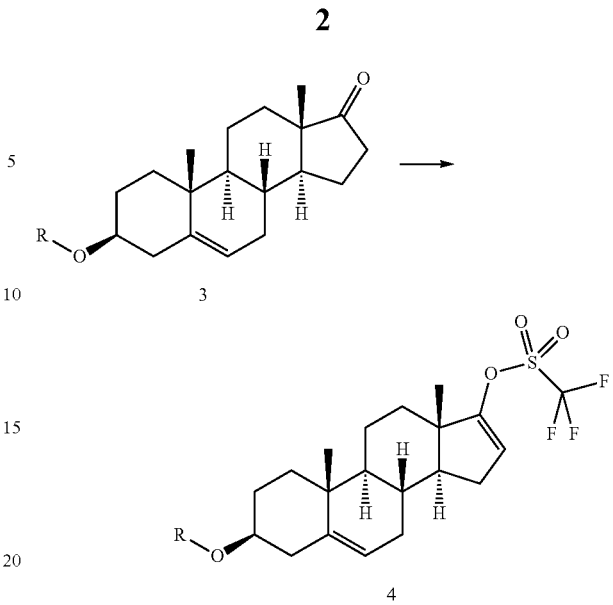

The preparation of Abiraterone acetate was originally disclosed in EP0633893 (BTG International Limited). The synthesis described in the experimental part involves the conversion of the carbonyl at the 17 position of prasterone acetate (3, R=COCH$_3$) to the corresponding enol triflate (4, R=COCH$_3$) by treatment with trifluoromethanesulphonic anhydride and 2,6-di-tert-butyl-4-methylpyridine. The use of said base, which among other things is rather expensive, involves the formation of an impurity deriving from the elimination of the acetate in the 3 position, which is difficult to remove without onerous chromatographic purifications. Subsequently, in WO2006/021777, BTG International Limited claimed the use of a series of bases which, as well as being more common and cheaper than 2,6-di-tert-butyl-4-methylpyridine, do not cause, or limit, the formation of said impurity.

The bases specified in the claim are pyridine, 2,6-lutidine, N-methylmorpholine, 1,4-diazabicyclo[2.2.2]octane (DABCO), trimethylamine, triethylamine, N,N-diisopropylethylamine (DIPEA), quinuclidine and 1,8-diaza-bicyclo-[5.4.0]-undec-7-ene (DBU), which are included in the more general definition of tertiary or heterocyclic amines with a pKa of the conjugate acid at 25° C. ranging between 5.12 and 12. The pKa range between 6.75 and 10.6, and in particular the use of lutidine and triethylamine, is preferred. As reported in WO2006/021777, the pKa range between 5.12 and 12, determined in aqueous solution, is critical to ensure the good result of the triflation reaction, and when bases with a comparatively low pKa of the conjugate acid (less than 5.21) are used, parallel reactions take place, with the formation of critical impurities or degradation products. This applies, for example, to 2,6-di-tert-butyl-4-methylpyridine (pKa 4.41), 2,6-di-tert-butylpyridine (pKa 4.95) and N,N-diethylaniline. For this latter base, the authors report a pKa value of the conjugate acid of 5.20, whereas higher values are reported in the literature.

DESCRIPTION OF THE INVENTION

We have surprisingly found that esters of nicotinic acid with C1-C4 alcohols, in particular methyl nicotinate (methyl 3-pyridinecarboxylate) and ethyl nicotinate (ethyl 3-pyridinecarboxylate), whose conjugate acids in water have a pKa of about 3.2, can be employed in the reaction used to convert products of formula 3 to products of formula 4 with high yields and high purity.

The object of the present invention is therefore a process for the conversion of a compound of formula 3, wherein R is an acetyl group or an alcohol (hydroxyl) protecting group, to a compound of formula 4 wherein R is as defined above, comprising reacting 3 with a triflating agent in the presence of a C1-C4 alkyl nicotinate, preferably methyl or ethyl nicotinate. The product 4 thus obtained can be conveniently used in a process for the preparation of Abiraterone or Abiraterone acetate.

DETAILED DESCRIPTION OF THE INVENTION

The conversion of ketones to vinyl triflates is a reaction well known in the literature, and typically requires the presence of a base and a triflating agent. In the case of preparation of vinyl triflates from steroid derivatives with a carbonyl function at the 17 position, the prior art is fully described in the above-mentioned document WO2006/021777, which discloses the use of an organic base wherein the pKa of the conjugate acid is between 5.21 and 12.

To the best of our knowledge there are no precedents for the use of methyl or ethyl nicotinate, or any other nicotinic acid ester, in the conversion reaction of ketones to vinyl triflates, and in the light of document WO2006/021777 the use of a similar base in the triflation reaction of steroidal ketones cannot be considered, as the pKa value of the conjugate acid in aqueous solution is too low. In fact, methyl and ethyl nicotinate have a pKa about 2 units lower than the minimum limit considered in WO2006/021777 to give efficient triflation {methyl nicotinate: pKa=3.15 [J. Am. Chem. Soc. 128, 351 (2006)]; ethyl nicotinate: pKa=3.22 [J. Chem. Soc. B, 727-730 (1970)]}. The efficiency of said bases in the triflation reaction is therefore entirely unexpected.

Methyl and ethyl nicotinate are cheap products, readily available on the market, and characterised by very low toxicity [methyl nicotinate: LDLo>2 g/kg (mouse), RTECS)].

Moreover, methyl and ethyl nicotinate do not give the collateral reactions with triflic anhydride that are described for lutidine [Journal of Organic Chemistry 48, 1776-7 (1983)], a preferred base in document WO2006/021777.

The object of the present patent application is the use of esters of nicotinic acid with C1-C4 alcohols in the presence of a triflating agent for the conversion of prasterone derivatives of formula 3 to the corresponding vinyl triflates of formula 4, wherein R is an acetyl group or an alcohol (hydroxyl) protecting group. Examples of esters of nicotinic acid with C1-C4 alcohols are methyl, ethyl, n-propyl, i-propyl and n-butyl nicotinate. Methyl and ethyl nicotinate are preferred. The preferred protecting groups are trifluoroacetyl, trichloroacetyl and formyl.

The preferred triflating agents include trifluoromethanesulphonic anhydride or an imide such as N-(2-pyridyl)triflimide or N-phenyltriflimide; trifluoromethanesulphonic anhydride is particularly preferred.

The preferred solvents are hydrocarbons, more preferably halogenated hydrocarbons such as methylene chloride, chloroform, 1,1-dichloroethane, 1,2-dichloroethane, chlorobutane or mixtures thereof.

The reaction is effected at a temperature ranging from −70° C. to +30° C., preferably from −30° C. to +20° C., and the reaction time ranges from 1 to 20 h, preferably from 3 to 10 h.

Conversion values above 90% and molar yields above 80% are typically obtained.

The reaction mixture is preferably quenched with water or acid or basic aqueous solutions. The organic phase can be used directly, "as is" or after concentration, for the next step, or the triflates of formula 4 can be isolated by crystallisation as described below.

Particularly preferred conditions for the triflation reaction are as follows:
triflating agent: trifluoromethanesulphonic anhydride (1.0 to 1.5 equivalents)
base: methyl or ethyl nicotinate (0.75 to 1.5 equivalents)
solvent: methylene chloride.

Said equivalents of the triflating agent and base are expressed in relation to 1 equivalent of the compound of formula 3.

To minimise the formation of impurities, the base is conveniently added to the reaction mixture, typically in a time ranging between 1 and 5 hours, after the addition of the triflating agent. Operating under these conditions, optimum conversion of prasterone trifluoroacetate and a triflate intermediate of high purity are obtained. Reducing the reaction temperature reduces the formation of impurities.

The low impurity profile of the organic phase containing the triflates of formula 4 enables them to be isolated by crystallisation. After the concentration of the organic phase, they can be crystallised by adding an organic solvent, preferably an alcohol such as methanol, or a mixture of solvents. The products thus obtained usually have a purity exceeding 90%.

The products of formula 3 are known products, and can be prepared by known techniques from prasterone (dehydroepiandrosterone), a commercially available intermediate widely used in the production of steroid derivatives.

The triflates of formula 4 can be used in a process for the preparation of Abiraterone or Abiraterone acetate by known methods, for example as described in EP0633893. Said use represents a further object of the invention.

The invention is further illustrated by the following examples.

EXAMPLE 1

Synthesis of Prasterone Trifluoroacetate Triflate (Compound of Formula 4 wherein R=$CF_3CO$) with Ethyl Nicotinate Trifluoromethanesulphonic anhydride (14.8 mL) is added in about 25 minutes to a solution of prasterone trifluoroacetate (30 g) in methylene chloride (540 mL), cooled to −10° C. The temperature is maintained at −8±2° C., and a solution of ethyl nicotinate (10.7 mL) in methylene chloride (60 mL) is added dropwise in 4 hours; the resulting mixture is left under stirring for about 24 h from the start of addition of triflic anhydride (HPLC control). After adding cold water (375 mL; 0-2° C.) without exceeding the temperature of 10° C., the organic phase is separated and washed with cold water (330 mL) and then with a 20% aqueous solution of sodium chloride (330 mL) The organic phase is then concentrated under vacuum (max bath temperature 25° C.), and a solvent change is effected with methanol until a residual volume of 120 mL is obtained. Acetonitrile (60 mL) is then added dropwise in 30 minutes at room temperature, and the suspension is cooled to 0° C. The crystal is left to grow for 1 h at 0° C., and the mixture is then filtered, washing the panel with cold methanol (30 mL; 0-2° C.). After drying under vacuum at 30° C. for 8 hours. 30 g of prasterone trifluoroacetate triflate is obtained.

EXAMPLE 2

Synthesis of Abiraterone

In an inert gas environment, diethyl(3-pyridyl)borane (8.8 g), bis(triphenylphosphine)palladium II dichloride (200 mg) and a 2M sodium carbonate aqueous solution (95 mL) are added to a solution of prasterone trifluoroacetate triflate prepared as described in example 1 (30 g) in tetrahydrofuran (300 mL) The resulting mixture is heated at 47° C. for about 18 h and then concentrated to half volume. The resulting suspension is cooled to 0-5° C. and filtered. The wet product is taken up in 300 mL of water at 45° C. for 1 h and then filtered. After drying, 16 g of Abiraterone is obtained.

EXAMPLE 3

Synthesis of Abiraterone Acetate

Acetic anhydride (70 g) is added to a suspension of Abiraterone (16 g) in ethyl acetate (48 mL) The mixture is heated to 70° C. until the reaction is complete (about 20 h); the temperature is then reduced to about 50° C. and methanol (28 mL) is added. The resulting mixture is maintained under stirring for 2 h, cooled to room temperature, and ethyl acetate (110 mL) and an aqueous solution of sodium carbonate (450 mL) are added. The phases are separated and the organic phase is treated with decolourising carbon. The organic phase is then concentrated under vacuum and the concentrate is taken up with acetonitrile (about 80 mL) to obtain a sandy solid, which is isolated by filtration (at 0-5° C.) and dried under vacuum at 40° C. for 8 h (about 15 g).

EXAMPLE 4

Synthesis of Prasterone Acetate Triflate with Methyl Nicotinate

Trifluoromethanesulphonic anhydride (17.2 mL) is added in about 25 minutes to a solution of prasterone acetate (30 g) in methylene chloride (540 mL), cooled to −10°. The temperature is maintained at −10±2° C. and a solution of methyl nicotinate (12.5 g) in methylene chloride (60 mL) is added dropwise in 4 hours; the resulting mixture is left under stirring for about 12 h from the start of addition of triflic anhydride (HPLC control). After adding cold water (375 mL; 0-2° C.) without exceeding the temperature of 10° C., the organic phase is separated and washed with cold aqueous solution (330 mL) and then with a 20% aqueous solution of sodium chloride (330 mL) The organic phase is then concentrated under vacuum and the residue is crystallised by treatment with a methanol/acetonitrile mixture at 0° C., then dried under vacuum at 30° C. to obtain 21.5 g of prasterone acetate triflate.

EXAMPLE 5

Synthesis of Crude Abiraterone Acetate

In an inert gas environment, diethyl(3-pyridyl)borane (7.5 g), bis(triphenylphosphine)palladium II dichloride (333 mg) and a 2M aqueous solution of sodium carbonate (80 mL) are added to a solution of prasterone acetate triflate prepared as described in example 4 (21.5 g) in tetrahydrofuran (306 mL) The resulting mixture is heated to reflux for about 2 h, then cooled to room temperature, and water (215 mL) and ethyl acetate (215 mL) are added. The phases are separated and the organic phase is treated with decolourising carbon. The decolourised organic phase is concentrated under vacuum to obtain crude Abiraterone acetate as oil (Abiraterone acetate content about 17 g).

EXAMPLE 6

Synthesis of Abiraterone Acetate Sulphate

40% sulphuric acid (8.2 mL) is added in about 30 minutes to a solution of crude Abiraterone acetate obtained as described in example 5 (Abiraterone acetate content about 17 g) in isopropyl acetate (140 mL) The precipitate is left under stirring at room temperature for 1 h and then filtered. The resulting residue is dried under vacuum at 40° C. for 12 hours. 21.4 g of Abiraterone acetate sulphate is obtained.

EXAMPLE 7

Synthesis of Prasterone Acetate Triflate with Ethyl Nicotinate

Trifluoromethanesulphonic anhydride (8.6 mL) is added in about 25 minutes to a solution of prasterone acetate (15 g) in methylene chloride (270 mL), cooled to −10°. The temperature is maintained at −10±2° C. and a solution of ethyl nicotinate (6.2 mL) in methylene chloride (30 mL) is added dropwise in 4 hours; the resulting mixture is left under stirring for about 12 h from the start of addition of triflic anhydride (HPLC control). After adding cold water (190 mL), the organic phase is separated and washed with water (150 mL) and then with a 20% aqueous solution of sodium chloride (150 mL) The organic phase is then concentrated under vacuum to an oily residue (prasterone acetate triflate content about 12.6 g), which is used "as is" for the synthesis of Abiraterone acetate.

EXAMPLE 8

Synthesis of Crude Abiraterone Acetate

In an inert gas environment, diethyl(3-pyridyl)borane (4.4 g), bis(triphenylphosphine)palladium II dichloride (0.15 g) and a 2M aqueous solution of sodium carbonate (50 mL) are added to a solution of prasterone acetate triflate prepared as described in example 7 (12.6 g) in tetrahydrofuran (180 mL) The resulting mixture is heated to reflux for about 2 h, then cooled to room temperature, and water (120 mL) and ethyl acetate (120 mL) are added. The phases are separated and the organic phase is treated with decolourising carbon. The decolourised organic phase is concentrated under vacuum to obtain crude Abiraterone acetate as oil (Abiraterone acetate content about 10 g), which is purified by treatment with polymer resin (DIAION HP20ss) eluting with acetonitrile—IPA—10 mM ammonium acetate buffer mixtures. The fractions containing the product with a purity exceeding 99.5% (HPLC monitoring) are combined and concentrated. The precipitate is filtered, washed with water and dried under vacuum (12 h, 40° C.) to obtain Abiraterone acetate as a white crystalline solid (8.8 g).

The invention claimed is:
1. A process for the conversion of a compound of formula 3,

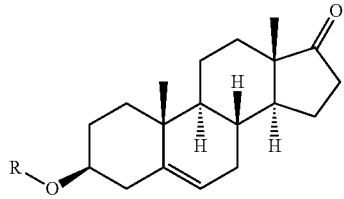

wherein R is an acetyl group or an alcohol-protecting group, to a compound of formula 4

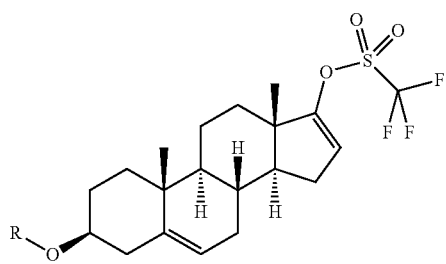

wherein R is as defined above, comprising the reaction of 3 with a triflating agent in the presence of a $C_1$-$C_4$ alkyl nicotinate (3-pyridinecarboxylate),
and wherein the triflating agent is trifluoromethanesulphonic anhydride.

2. The process according to claim 1, wherein the $C_1$-$C_4$ alkyl nicotinate is methyl or ethyl nicotinate.

3. The process according to claim 1 wherein R is an acetyl group.

4. The process according to claim 1 wherein R is a trifluoroacetyl group.

5. The process according to claim 1 wherein the conversion of compound 3 to 4 is performed in a halogenated hydrocarbon as solvent, at a temperature ranging between −70° C. and +30° C. and for a reaction time ranging between 1 and 20 h.

6. The process according to claim 5 wherein the halogenated hydrocarbon is selected from methylene chloride, chloroform, 1,1-dichloroethane, 1,2-dichloroethane, chlorobutane and mixtures thereof.

7. The process according to claim 6 wherein the halogenated hydrocarbon is methylene chloride, and 1.0 to 1.5 equivalents of trifluoromethanesulphonic anhydride and 0.75 to 1.5 equivalents of methyl or ethyl nicotinate are used to 1 equivalent of a compound of formula 3.

8. A process for the preparation of Abiraterone or Abiraterone acetate comprising the process of claim 1.

* * * * *